United States Patent
Gulati

(10) Patent No.: US 9,493,524 B2
(45) Date of Patent: *Nov. 15, 2016

(54) METHODS FOR TREATMENT OF STROKE OR CEREBROVASCULAR ACCIDENTS USING AN $ET_B$ RECEPTOR AGONIST

(71) Applicant: MIDWESTERN UNIVERSITY, Downers Grove, IL (US)

(72) Inventor: Anil Gulati, Naperville, IL (US)

(73) Assignee: MIDWESTERN UNIVERSITY, Downers Grove, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/149,785

(22) Filed: Jan. 7, 2014

(65) Prior Publication Data
US 2014/0193393 A1    Jul. 10, 2014

Related U.S. Application Data

(63) Continuation of application No. 12/673,140, filed as application No. PCT/US2008/073581 on Aug. 19, 2008, now Pat. No. 8,623,823.

(60) Provisional application No. 60/965,591, filed on Aug. 21, 2007.

(51) Int. Cl.
| | |
|---|---|
| A61K 38/22 | (2006.01) |
| A61P 9/10 | (2006.01) |
| C07K 14/47 | (2006.01) |
| A61K 38/18 | (2006.01) |
| A61K 38/49 | (2006.01) |
| A61K 31/42 | (2006.01) |
| A61K 38/17 | (2006.01) |
| A61K 45/06 | (2006.01) |
| C07K 14/575 | (2006.01) |

(52) U.S. Cl.
CPC ............. *C07K 14/47* (2013.01); *A61K 31/42* (2013.01); *A61K 38/1709* (2013.01); *A61K 38/1808* (2013.01); *A61K 38/2285* (2013.01); *A61K 38/49* (2013.01); *A61K 45/06* (2013.01); *C07K 14/57536* (2013.01)

(58) Field of Classification Search
None
See application file for complete search history.

(56) References Cited

U.S. PATENT DOCUMENTS

| | | | |
|---|---|---|---|
| 5,055,470 A | 10/1991 | Boissard et al. | |
| 2003/0104976 A1 | 6/2003 | Davar et al. | |
| 2004/0138121 A1 | 7/2004 | Gulati | |

FOREIGN PATENT DOCUMENTS

| | | |
|---|---|---|
| EP | 0410114 A2 | 1/1991 |
| WO | WO-2004/037235 A2 | 5/2004 |

OTHER PUBLICATIONS

Wise et al, 2000. BMJ. 320: 823.*
Bell et al., Effect of endothelin-1 and sarafotoxin S6c on blood flow in a rat tumor, J. Cardiovasc. Pharmacol., 26(Suppl. 3):S222-5 (1995).
Bell et al., Modification of blood flow in the HSN tumour and normal tissues of the rat by the endothelin ETb receptor agonist, IRL 1620, Int. J. Cancer, 80:295-302 (1999).
Bomber et al., Propranolol hydrochloride enhancement of tumor perfusion and uptake of gallium-67 in a mouse sarcoma, J. Nucl. Med., 27(2):243-5 (1986).
Bork, Powers and pitfalls in sequence analysis: the 70% hurdle, Genome Res., 10(4):398-400 (2000).
Brasch et al., Assessing tumor angiogenesis using macromolecular MR imaging contrast media, JMRI, 7:68-74 (1997).
Brenner, Errors in genome annotation, Trends in Genetics, 15(4):132-3 (1999).
Briyal, S., et al., Effect of Combination of Endothelin Receptor Antagonist (TAK-044) and Aspirin in Middle Cerebral Artery Occlusion Model of Acute Ischemic Stroke in Rats, Methods and Findings in Experimental and Clinical Pharmacology, May 2007, vol. 29, No. 4, pp. 257-263.
Brooks et al., Identification and function of putative ETB receptor subtypes in the dog kidney, J. Cardiovasc. Pharmacol., 26(Suppl 3):S322-5 (1995).
Chuquet, J., et al., Selective Blockade of Endothelin-B Receptors Exacerbates Ischemic Brain Damage in the Rat, Stroke, Journal of the American Heart Association, Dec. 2002, vol. 33, No. 12, pp. 3019-3025.
Doerks et al., Protein annotation: detective work for function prediction, Trends Genet., 14(6):248-50 (1998).
Graf et al., Determination of optimal time window for liver scanning with CT during arterial portography, Radiology, 190:43-7 (1994).
Harvey et al., Imaging of tumour therapy responses by dynamic CT, Eur. J. Radiology, 30:221-6 (1999).
International Search Report in international application No. PCT/US2008/073581, dated Jul. 15, 2009.
Ishizuka et al., Endothelin-1 enhances vascular cell adhesion molecule-1 expression in tumor necrosis factor alpha-stimulated vascular endothelial cells, Eur. J. Pharmacol., 369(2):237-45 (1999).
Katayama, Current trends in the treatment of acute ischemic stroke, Nichiidaishi, 65(3):4-9 (1999).
Muruganandham et al., Diltiazem enhances tumor blood flow: MRI study in a murine tumor, Int. J. Radiation Oncology Biol. Phys., 43(2):413-21 (1999).
Ngo et al., The Protein Folding Problem and Tertiary Structure Prediction, Chapter 14 in Computational Complexity Protein Structure Prediction and the Levinthal Paradox, pp. 492-495 (1995).
Nv et al., N-Suc-[Glu9, Ala11, 15]ET-1(8-21) increases blood perfusion and enhances paclitaxel delivery to the tumor, 96th Annual Meeting of the American Association for Cancer Research, Abstract 5741 (2005).

(Continued)

*Primary Examiner* — Zachary Howard
(74) *Attorney, Agent, or Firm* — Marshall, Gerstein & Borun LLP

(57) ABSTRACT

Methods of using an $ET_B$ receptor agonist, such as IRL-1620, for the treatment of stroke or cerebrovascular accidents are disclosed. The $ET_B$ receptor agonist is used alone or in combination with a second agent useful in the treatment of stroke or other cerebrovascular accident.

18 Claims, 9 Drawing Sheets

(56) References Cited

OTHER PUBLICATIONS

Patel et al., Endothelin receptor mediated constriction and dilatation in feline cerebral resistance arterioles in vivo, Eur. J. Pharmacol., 307:41-8 (1996).

Phillips, The challenge of gene therapy and DNA delivery, J. Pharm. Pharmacol., 53(9):116-974 (2001).

Rai et al., Evidence for the involvement of ET(B) receptors in ET-1-induced changes in blood flow to the rat breast tumor, Cancer Chemother. Pharmacol., 51(1):21-8 (2003).

Recht et al., The sequencing of chemotherapy and radiation therapy after conservative surgery for early-stage breast cancer, NEJM, 334(21):1356-61 (1996).

Sardanelli et al., Dynamic helical CT of breast tumors, J. Comp. Assisted Tomography, 22(3):398-407 (1998).

Skolnick et al., From genes to protein structure and function: novel applications of computational approaches in the genomic era, Trends Biotechnol., 18(1):34-9 (2000).

Smyth et al., Use of vasoactive agents to increase tumor perfusion and the antitumor efficacy of drug-monoclonal antibody conjugates, J. Natl. Cancer Inst., 79(6):1367-73 (1987).

Sonveaux et al., Endothelin-1 is a critical mediator of myogenic tone in tumor arterioles: implications for cancer treatment, Cancer Res., 64(9):3209-14 (2004).

Takagawa et al., Efficacy of the drugs administered to the patients with cerebral vascular diseases from a viewpoint of cerebral blood flow measurement, 48(9):667-93 (1994).

Wells, Additivity of mutational effects in proteins, Biochem., 29(37):8509-17 (1990).

Wu, Recent discovery and development of endothelin receptor antagonists, Exp. Opin. Ther. Patents, 10(11):1653-68 (2000).

Yagami et al., Effects of an endothelin B receptor agonist on secretory phospholipase A2-IIA-induced apoptosis in cortical neurons, Neuropharmacology, 48(2):291-300 (2005).

Zuccarello, M., et al., Endothelin B Receptor Antagonists Attenuate Subarachnoid Hemorrhage-Induced Cerebral Vasospasm, Stroke, Journal of the American Heart Association, Sep. 1998, vol. 29, No. 9, pp. 1924-1929.

Gulati, et al. "Effect of centrally administered endothelin agonists on systemic and regional blood circulation in the rat: role of sympathetic nervous system" Neuropeptides 31(4):301-309 (1997).

Yagami, et al. "Effects of endothelin B receptor agonists of amyloid β protein (25-35)-induced neuronal cell death," Brain Research 948:72-81 (2002).

\* cited by examiner

FIG. 1

SEQ ID NO:1 (Amino acid sequence of IRL-1620):

Suc-Asp-Glu-Glu-Ala-Val-Tyr-Phe-Ala-His-Leu-Asp-Ile-Ile-Trp

SEQUENCE LISTING

<160> NUMBER OF SEQ ID NOS: 5

<210> SEQ ID NO 1
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: Succinyl group at N-terminus

<400> SEQUENCE: 1

Asp Glu Glu Ala Val Tyr Phe Ala His Leu Asp Ile Ile Trp
1               5                   10

<210> SEQ ID NO 2
<211> LENGTH: 21
<212> TYPE: PRT
<213> ORGANISM: Artificial Sequence
<220> FEATURE:
<223> OTHER INFORMATION: Synthetic polypeptide
<220> FEATURE:
<221> NAME/KEY: DISULFID
<222> LOCATION: (1)..(15)
<223> OTHER INFORMATION: Disulfide bridge between residues 1 and 15

```
<220> FEATURE:
<221> NAME/KEY: DISULFID
<222> LOCATION: (3)..(11)
<223> OTHER INFORMATION: Disulfide bridge between residues 3 and 11

<400> SEQUENCE: 2

Cys Thr Cys Asn Asp Met Thr Asp Glu Glu Cys Leu Asn Phe Cys His
1               5                   10                  15

Gln Asp Val Ile Trp
            20

<210> SEQ ID NO 3
<211> LENGTH: 21
<212> TYPE: PRT
<213> ORGANISM: Artificial Sequence
<220> FEATURE:
<223> OTHER INFORMATION: Synthetic polypeptide
<220> FEATURE:
<221> NAME/KEY: DISULFID
<222> LOCATION: (1)..(15)
<223> OTHER INFORMATION: Disulfide bridge between residues 1 and 15
<220> FEATURE:
<221> NAME/KEY: DISULFID
<222> LOCATION: (3)..(11)
<223> OTHER INFORMATION: Disulfide bridge between residues 3 and 11

<400> SEQUENCE: 3

Cys Thr Cys Phe Thr Tyr Lys Asp Lys Glu Cys Val Tyr Tyr Cys His
1               5                   10                  15

Leu Asp Ile Ile Trp
            20

<210> SEQ ID NO 4
<211> LENGTH: 16
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: Acetyl group at N-terminus

<400> SEQUENCE: 4

Leu Met Asp Lys Glu Ala Val Tyr Phe Ala His Leu Asp Ile Ile Trp
1               5                   10                  15

<210> SEQ ID NO 5
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 5

Ala Ser Ala Ser Ser Leu Met Asp Lys Glu Ala Val Tyr Phe Ala His
1               5                   10                  15

Leu Asp Ile Ile Trp
            20
```

METHODS FOR TREATMENT OF STROKE OR CEREBROVASCULAR ACCIDENTS USING AN $ET_B$ RECEPTOR AGONIST

CROSS-REFERENCE TO RELATED APPLICATION

This application is a continuation of U.S. application Ser. No. 12/673,140, filed Dec. 6, 2011, now U.S. Pat. No. 8,623,823, incorporated herein by reference, which is a U.S. National Phase of International Application No. PCT/US08/73581 filed Aug. 19, 2008, incorporated herein by reference, which claims the benefit of U.S. Provisional Patent Application No. 60/965,591, filed Aug. 21, 2007, incorporated herein by reference.

FEDERALLY SPONSORED RESEARCH OR DEVELOPMENT

None.

FIELD OF THE INVENTION

The present invention relates to methods of using an endothelin$_B$ ($ET_B$) receptor agonist, such as IRL-1620, for the treatment of stroke and cerebrovascular accidents caused, for example, by thrombosis, embolism, or hemorrhage. The $ET_B$ receptor agonist can be used alone or in combination with a thrombolytic agent, like tissue plasminogen activator, or an $ET_A$ antagonist, or an erythropoiesis-stimulating agent, like erythropoietin, darbepoetin, and epoetin alfa, or an oxygen carrier, like a hemoglobin-based blood substitute and a perfluorocarbon-based blood substitute. Other neuroprotective agents that can be used in combination with the $ET_B$ receptor agonist include argatroban, alfimeprase, tenecteplase, ancrod, sildenafil, insulin and its growth factor, magnesium sulfate, human serum albumin, caffeinol (combination of caffeine and alcohol), microplasmin, statins, eptifibatide, tinzaparin, enecadin, citicoline, edaravone, cilostazol, or hypothermia. Using an $ET_B$ receptor agonist, alone or in combination with an existing neuroprotective agent, provides blood supply, oxygenation, and reduces damage to brain cells.

BACKGROUND OF THE INVENTION

The discovery of endothelin-1 (ET-1), a 21-amino acid peptide, has helped improve knowledge of local regulation of vascular tone by blood vessels (M. Yanagisawa et al. (1988) *Nature* 332(6163):411-5). ET-1 is generated in endothelial cells and vascular smooth muscle cells via conversion of proET-1 to ET-1 in the presence of endothelin converting enzyme-1 (ECE-1). This conversion from proET-1 to ET-1 is essential for optimal vasoconstrictor activity of ET-1 (M. Yanagisawa et al. (1988) *Nature* 332(6163):411-5 and G. D. Johnson et al. (1999) *J Biol Chem* 274(7):4053-8).

ET-1 is released from cultured endothelial cells at a slow basal rate. Due to a high vasoconstrictor potency and long lasting action, the continuous release of small amounts of ET-1 from endothelial cells towards the underlying smooth muscle cells may contribute to the maintenance of vascular tone and blood pressure (T. Miyauchi et al. (1999) *Annu Rev Physiol* 61:391-415). Under physiological conditions, the basal tone maintained by ET-1 is balanced by the release of endothelium derived relaxing factor (EDRF or nitric oxide and prostacyclin) and vasoconstrictor substances (thromboxane) (E. L. Schiffrin (1994) *Clin Invest Med* 17(6):602-20 and P. B. Persson (1996) *Physiol Rev* 76(1):193-244).

ET and its axis (ET-1, ET-2, ET-3, $ET_A$ and $ET_B$ receptors) have triggered considerable efforts to develop ET receptor antagonists having therapeutic potential in treating diseases like hypertension, heart failure, renal diseases, and cancer (A. Gulati et al. (1992) *Drug Develop Res* 26:361-387; A. Gulati et al. (1997) *Neuropeptides* 31(4) 301-9; G. Remuzzi et al. (2002) *Nat Rev Drug Discov* 1(12):986-1001; J. Nelson et al. (2003) *Nat Rev Cancer* 3(2):110-6; and A. Gulati et al. (2004) *J Cardiovasc Pharmacol* 44:S483-S486). Several $ET_A$ receptor antagonists, e.g., atrasentan, avosentan, clazosentan, darusentan, sitaxsentan, and ZD4054, are in mid to late stage clinical trial. Bosentan, a non-specific $ET_A$ and $ET_B$ receptor antagonist, has been marketed for a few years, and ambrisentan ($ET_A$ receptor antagonist) recently was approved for sale by the U.S. Food and Drug Administration (FDA) for a once-daily treatment of pulmonary arterial hypertension.

Intense efforts are devoted to develop $ET_A$ receptor antagonists. However, virtually no effort has been expended to develop ET agonists as therapeutic agents. The first proposed therapeutic use of an $ET_B$ receptor agonist resulted from a discovery that IRL-1620, a potent $ET_B$ receptor agonist, selectively enhanced breast tumor perfusion in rats (A. Rai et al. (2003) *Cancer Chemother Pharmacol* 51(1):21-8; A. Gulati (2003) U.S. Patent Publication 2004/0138121; and A. Gulati (2006) U.S. Patent Publication 2006/0211617). Administration of BQ788, a highly selective $ET_B$ receptor antagonist, blocked the tumor perfusion induced by IRL-1620 and confirmed the involvement of $ET_B$ receptors in tumor vasodilation (A. Rai et al. (2005) *J Pharm Pharmacol* 57(7):869-76 and N. V. Rajeshkumar et al. (2005) *Breast Cancer Research and Treatment* 94(3):237-247). The selective enhancement of tumor blood flow resulted in a greater percentage of infused paclitaxel reaching the tumor as compared to the normal tissues.

In a study conducted in breast tumor rats, IRL-1620 administration prior to paclitaxel resulted in a significant reduction of tumor volume, as well as a 20% complete remission of tumors, compared to paclitaxel treated rats (A. Rai et al. (2005) *J Pharm Pharmacol* 57(7):869-76. and N. V. Rajeshkumar et al. (2005) *Breast Cancer Research and Treatment* 94(3):237-247). See United States Patent Publication Nos. 2004/0138121, 2006/0211617, 2006/0257362, and 2007/0032422.

The present invention is directed to a new use for $ET_B$ receptor agonists, including IRL-1620, in the treatment of stroke and other cerebrovascular accidents. In particular, it now has been found that an $ET_B$ receptor agonist significantly increases cerebral blood perfusion, which is a novel and unexpected finding.

ETs are widely distributed throughout the body and are involved in a variety of physiological functions (A. Gulati et al. (1992) *Drug Develop Res* 26:361-387 and J. Nelson et al. (2003) *Nat Rev Cancer* 3(2):110-6). ETs exert their effects by binding to two distinct types of cell surface receptors, $ET_A$ and $ET_B$. $ET_A$ receptors have equal affinity for ET-1 and ET-2, and low affinity for ET-3. $ET_B$ receptors have equal affinity for ET-1, ET-2, and ET-3. Pharmacological evidence suggests that $ET_B$ receptors can be divided into two subtypes, i.e., $ET_{B1}$ receptors present on endothelial cells and $ET_{B2}$ receptors present on smooth muscle cells (D. P. Brooks et al. (1995) *J Cardiovasc Pharmacol* 26 Suppl 3:S322-5 and A. Leite-Moreira et al. (2004) *Am J Physiol Heart Circ Physiol* 287(3):H1194-9). Both $ET_A$ and $ET_B$ receptors belong to the G protein-coupled receptor (GPCR) family (J.

Nelson et al. (2003) *Nat Rev Cancer* 3(2):110-6). $ET_A$ and $ET_B$ receptors located on vascular smooth muscle cells, produce vasoconstriction, whereas $ET_B$ receptors present on endothelial cells are mainly vasodilatory (G. Remuzzi et al. (2002) *Nat Rev Drug Discov* 1(12):986-1001).

IRL-1620 (N-Succinyl-[Glu$^9$, Ala$^{11,15}$] Endothelin 1) is a synthetic analogue of ET-1, i.e., a fragment of ET-1 having amino acids 8-21 of ET-1. IRL-1620 is a highly selective endothelin B receptor agonist, being 120,000 times more selective to $ET_B$ receptors than to $ET_A$ receptors (M. Takai et al. (1992) *Biochem Biophys Res Commun* 184(2):953-9). IRL-1620 has a molecular formula of $C_{86}H_{117}N_{17}O_{27}$ and a molecular weight of 1820.95. The molecular structure of IRL-1620, as illustrated in FIG. 1, is an amino acid sequence of Suc-Asp-Glu-Glu-Ala-Val-Tyr-Phe-Ala-His-Leu-Asp-Ile-Ile-Trp (SEQ ID NO:1).

Pharmacological Effects of IRL-1620

IRL-1620, like endothelins, can produce both vasodilation and vasoconstriction. Interaction of IRL-1620 with $ET_B$ receptors on endothelial cells leads to vasodilation, whereas an interaction with $ET_B$ receptors on smooth muscle cells leads to vasoconstriction. Furthermore, primary activation of $ET_B$ receptors by IRL-1620 can lead to autocrine/paracrine ET-1 release that subsequently activates both $ET_A$ and $ET_B$ receptors (S. Noguchi, et al. (1996) *Br J Pharmacol* 118(6):1397-402). Thus, the net effect of IRL-1620 is related to a number of factors, including the type of tissue, the species, and the physiological conditions. There have been a number of studies on pharmacological effects of IRL-1620 because it is a highly selective agonist of $ET_B$ receptors and often is used to delineate the role of $ET_B$ receptors in a given physiological situation. Some of these studies summarized below show that the vasoconstrictive effects of IRL-1620 are much less pronounced than those of ET-1. Other $ET_B$ receptor agonists known to persons skilled in the art produce pharmacological effects similar to those of IRL-1620, with the net effect also being related to the ability of a specific compound to selectively agonize $ET_B$ receptors.

Systemic Hemodynamic Effects

IRL-1620 exhibits systemic hemodynamic effects, including transient vasodilation and sustained vasoconstriction, in anesthetized rats (B. Palacios et al. (1997) *Br J Pharmacol* 122(6):993-8 and S. W. Leung et al. (2002) *J Cardiovasc Pharmacol* 39(4):533-43), in an open-chest rat model (M. E. Beyer et al. (1995) *J Cardiovasc Pharmacol* 26 Suppl 3:S150-2), and in normal and cardiomyopathic hamsters (J. C. Honore et al. (2002) *Clin Sci (Lond)* 103 Suppl 48:280S-283S). The vasoconstrictive effects of IRL-1620 are less pronounced compared to those of ET-1 (Palacios et al. (1997) *Br J Pharmacol* 122(6):993-8; J. C. Honore et al. (2002) *Clin Sci (Lond)* 103 Suppl 48:280S-283S; and S. W. Leung et al. (2002) *J Cardiovasc Pharmacol* 39(4):533-43) and IRL-1620 had a positive inotropic effect (M. E. Beyer et al. (1995) *J Cardiovasc Pharmacol* 26 Suppl 3:S150-2).

Regional Hemodynamic Effects

IRL-1620 causes renal vasodilation in anesthetized dogs upon intrarenal arterial perfusion (T. Yukimura et al. (1994) *Eur J Pharmacol* 264(3):399-405) and pulmonary vasodilation in neonatal lambs upon intrapulmonary arterial injection (J. Wong et al. (1995) *J Cardiovasc Pharmacol* 25(2):207-15). A pulmonary vasodilatory effect of IRL-1620 also is observed in isolated perfused rat lungs (M. Muramatsu et al. (1999) *Am J Physiol* 276(2 Pt 1):L358-64). Injection of IRL-1620 into the circumflex coronary artery of anesthetized goats does not cause coronary vasoconstriction, whereas ET-1 administered similarly caused coronary vasoconstriction (J. L. Garcia et al. (1996) *Eur J Pharmacol* 315(2):179-86).

Effect on Respiratory Airway Smooth Muscles

Intravenous administration of IRL-1620 to anesthetized, artificially-ventilated guinea pigs resulted in bronchoconstriction in a biphasic manner (S. Noguchi et al. (1996) *Br J Pharmacol* 118(6):1397-402). The second phase of bronchoconstriction probably is due to the activation of $ET_B$ receptors by IRL-1620 leading to autocrine/paracrine release of ET-1 that subsequently activated both $ET_A$ and $ET_B$ receptors (S. Noguchi et al. (1996) *Br J Pharmacol* 118(6):1397-402).

Experimental Studies on Human Tissues

In vitro, IRL-1620 causes contraction of human internal mammary arterial segments, but not human radial arterial segments (J. J. Liu, et al. (1996) *Clin Sci (Lond)* 90(2):91-6). The contractile effect of IRL-1620 on internal mammary arteries reached a maximum of 20% of that obtained with ET-1 or noradrenaline. Further increases in concentration of IRL-1620 caused relaxation of the contracted arteries. IRL-1620 also had a contractile effect on human bronchial rings in a biphasic manner (T. Takahashi et al. (1997) *Eur J Pharmacol* 324(2-3):219-22).

Clinical Studies

To date, IRL-1620 has not been administered to humans. However, a phase I, open label, ascending dose study of the safety, tolerability, pharmacokinetics, and pharmacodynamics of IRL-1620 in patients with recurrent or progressive carcinoma (NCT00613691) is ongoing. Furthermore, a number of human studies have been conducted with ET-1, a much more potent vasoconstrictive agent than IRL-1620, as demonstrated in animal studies (B. Palacios et al. (1997) *Br J Pharmacol* 122(6):993-8 and S. W. Leung et al. (2002) *J Cardiovasc Pharmacol* 39(4):533-43). Administration of ET-1 to human subjects by perfusion at doses ranging from 1 to 20 ng/kg/min caused dose-dependent systemic vasoconstriction and consequential changes in hemodynamic parameters (D. Kiely et al. (1997) *Cardiovasc Res* 33(2):378-86; A. Franco-Cereceda et al. (1999) *Scand Cardiovasc J* 33(3):151-6; and F. Kiefer et al. (2000) *Exp Clin Endocrinol Diabetes* 108(5):378-81), but did not produce any serious adverse events.

Intravenous administration of ET-1 also causes coronary vasoconstriction (J. Pernow et al. (1996) *Circulation* 94(9):2077-82). However, coronary vasoconstriction may not be expected with IRL-1620 in humans. It has been shown that, in human coronary arteries, $ET_B$ receptors are absent or present at very low levels, and therefore, would make minimal contribution toward coronary vasoconstriction (W. A. Bax et al. (1994) *Br J Pharmacol* 113(4):1471-9; A. P. Davenport et al. (1995) *J Cardiovasc Pharmacol* 26 Suppl 3:S265-7; A. P. Davenport et al. (1994) *Br J Pharmacol* 111(1):4-6; W. A. Bax et al. (1993) *Naunyn Schmiedebergs Arch Pharmacol* 348(4):403-10; A. P. Davenport et al. (1995) *J Cardiovasc Pharmacol* 22 Suppl 8:522-5; and O. Saetrum Opgaard et al. (1996) *Regul Pept* 63(2-3):149-56).

Human studies also were conducted with an endothelin agonist, sarafotoxin S6c, which is less selective for $ET_B$ receptors than IRL-1620. On infusion into brachial artery, sarafotoxin S6c showed less reduction in forearm blood flow compared to ET-1 (W. G Haynes et al. (1995) *Circulation* 92(3): 357-63). Thus, any vasoconstrictive effects of IRL-1620 in humans are expected to be less than those observed with ET-1 and other endothelin agonists administered to humans to date.

Effect on Cerebral Blood Vessels

Endothelin has been implicated in a number of cerebrovascular disorders, including subarachnoid hemorrhage (R. Suzuki et al. (1992) *J Neurosurg* 77(1):96-100) and ischemic stroke (I. Ziv et al. (1992) *Stroke* 23(7):1014-6). It has been found that $ET_A$ receptor antagonists relieve chronic cerebral vasospasm (M. Clozel et al. (1993) *Life Sci* 52(9):825-34; S. Itoh et al. (1993) *Biochem Biophys Res Commun* 195(2): 969-75; H. Nirei et al. (1993) *Life Sci* 52(23):1869-74; and R. N. Willette et al. (1994) *Stroke* 25(12):2450-5; discussion 2456). Studies have been performed to characterize endothelin receptors in the cerebral blood vessels. $ET_A$ receptors were found to mediate contraction in human cerebral, meningeal, and temporal arteries (M. Adner et al. (1994) *J Auton Nerv Syst* 49 Suppl:S117-21) and a marked $ET_B$ receptor-mediated relaxation was obtained with ET-3 when $ET_A$ receptor activity was blocked using FR139317 (IUPAC Name: (2R)-2-[[(2R)-2-[[(2S)-2-(azepane-1-carbonylamino)-4-methylpentanoyl]amino]-3-(1-methylindol-3-yl)propanoyl]amino]-3-pyridin-2-ylpropanoic acid) in pre-contracted human temporal arteries (G. A. Lucas, et al. (1996). *Peptides* 17(7): 1139-44).

Overall, a need still exists in the art to identify agents, or combinations of agents, that effectively treat strokes and other cerebrovascular accidents. To date, no report exists on the effect of IRL-1620 on cerebral circulation, and the present disclosure is the first reporting that IRL-1620 increases cerebral blood perfusion, as measured with laser-Doppler perfusion method.

SUMMARY OF THE INVENTION

The present invention is directed to administration of an $ET_B$ receptor agonist in the treatment of strokes and other cardiovascular accidents. Accordingly, one embodiment of the present invention is to provide a method of treating strokes and other cerebrovascular accidents comprising administering to a mammal in need thereof a therapeutically effective amount of an $ET_B$ receptor agonist.

Another embodiment of the present invention is to provide a composition comprising an $ET_B$ receptor agonist useful in the treatment of strokes and other cerebrovascular accidents. In particular, the present invention is directed to compositions containing an $ET_B$ receptor agonist, and to methods of administering the composition to treat strokes and other cerebrovascular accidents. In yet another embodiment, the composition further comprises a pharmaceutically acceptable carrier.

Another embodiment of the present invention is to provide a composition comprising (a) an $ET_B$ receptor agonist, (b) a second therapeutic agent useful in the treatment of stroke or other cerebrovascular accident, and (c) an optional excipient and/or pharmaceutically acceptable carrier.

In a further embodiment, the invention provides for use of a composition comprising an $ET_B$ receptor agonist and an optional neuroprotective agent for the manufacture of a medicament for treating stroke and other cerebrovascular accidents in an individual in need thereof.

Still another embodiment of the present invention is to provide a kit for human pharmaceutical use, comprising (a) a container, (b1) a packaged composition comprising an $ET_B$ receptor agonist and, optionally, (b2) a packaged composition comprising a neuroprotective agent useful in the treatment of stroke or other cerebrovascular accident, and (c) a package insert containing directions for use of the composition or compositions, administered simultaneously or sequentially, in the treatment of stroke and/or other cerebrovascular accidents.

In one embodiment, the present invention provides a method of treating a patient with stroke or cerebrovascular accident comprising administering a therapeutically effective amount of an endothelin$_B$ ($ET_B$) receptor agonist to the patient in need thereof. The stroke or cerebrovascular accident can be caused, for example, by thrombosis, embolism, or hemorrhage. In one preferred embodiment, the $ET_B$ receptor agonist comprises N-Succinyl-[Glu$^9$, Ala$^{11,15}$] Endothelin 1 (i.e., IRL-1620).

The $ET_B$ receptor agonist can be administered alone, or in combination with a second therapeutic agent useful in a treatment of stroke or other cerebrovascular accident, such as one or more neuroprotective agent, like a thrombolytic agent (such as, but not limited to, tissue plasminogen activator), or an $ET_A$ antagonist, such as, but not limited to, sulfosoxazole, clazosentan, atrasentan, tezosentan, bosentan, sitaxsentan, enrasentan, BMS 207940, BMS 193884, BMS 182874, J 104132, VML 588/Ro 61 1790, T-0115, TAK 044, BQ 788, TBC2576, TBC3214, PD180988, ABT 546, SB247083, RPR118031A, and BQ123), an erythropoiesis-stimulating agent (such as erythropoietin, darbepoetin, and epoetin alfa), or an oxygen carrier (such as a hemoglobin-based blood substitute or a perfluorocarbon based blood substitute). Other neuroprotective agents that can be administered in combination with the $ET_B$ receptor agonist include, but are not limited to, argatroban, alfimeprase, tenecteplase, ancrod, sildenafil, insulin and its growth factor, magnesium sulfate, human serum albumin, caffeinol (combination of caffeine and alcohol), microplasmin, statins, eptifibatide, tinzaparin, enecadin, citicoline, edaravone, cilostazol, hypothermia, and mixtures thereof.

The $ET_B$ receptor agonist and the second therapeutic agent can be administered together as a single-unit dose or separately as multi-unit doses, wherein the $ET_B$ receptor agonist is administered before the second therapeutic agent or vice versa. It is envisioned that one or more dose of the $ET_B$ receptor agonist or one and/or more dose of the second therapeutic agent can be administered.

In an embodiment, the $ET_B$ receptor agonist and neuroprotective therapeutic agent are administered simultaneously. In related embodiments, the $ET_B$ receptor agonist and neuroprotective therapeutic agent are administered from a single composition or from separate compositions. In a further embodiment, the $ET_B$ receptor agonist and neuroprotective agent are administered sequentially. The $ET_B$ receptor agonist, as used in the present invention, can be administered in an amount of about 0.005 to about 500 micrograms per dose, about 0.05 to about 250 micrograms per dose, or about 0.5 to about 50 micrograms per dose. Alternatively, the $ET_B$ receptor agonist can be administered in an amount of about 0.005 to about 50 micrograms per kilogram per min infusion, or about 0.05 to about 5 micrograms per kilogram per min infusion.

These and other aspects and features of the present invention will become apparent from the following drawings and detailed description of the preferred embodiments.

BRIEF DESCRIPTION OF THE DRAWINGS

FIG. 1 illustrates the molecular structure of IRL-1620;

DETAILED DESCRIPTION OF THE PREFERRED EMBODIMENT

Figure 2:
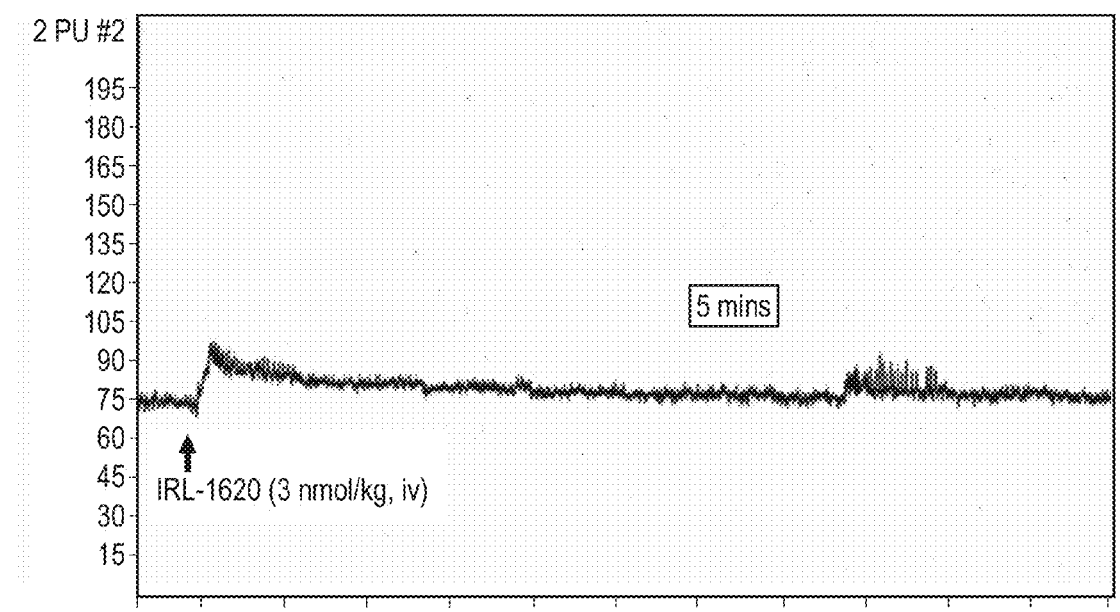
FIG. 2 shows the effect of IRL-1620 (3 nmol/kg, iv) on cerebral blood perfusion of urethane anesthetized rat using Laser Doppler Flowmetry, wherein IRL-1620 significantly increased cerebral blood perfusion compared to baseline.

The present invention is described in connection with preferred embodiments, however, it should be appreciated that the invention is not limited to the disclosed embodiments. It is understood that, given the above description of the embodiments of the invention, various modifications can be made by one skilled in the art. Such modifications are intended to be encompassed by the claims below.

As used herein, the terms "endothelin$_B$ receptor agonist", "$ET_B$ receptor agonist", and "$ET_B$ agonist" are used interchangeably.

As used herein, the terms "treat," "treating," "treatment," and the like refer to reducing or ameliorating a disorder and/or symptoms associated therewith. Although not precluded, treating a disorder or condition does not require that the disorder, condition or symptoms associated therewith be completely eliminated. As used herein, the terms "treat," "treating," "treatment," and the like may include "prophylactic treatment" which refers to reducing the probability of redeveloping a disorder or condition, or of a recurrence of a controlled disease or condition, in a subject who does not have, but is at risk of or is susceptible to redeveloping a disorder or condition or a recurrence of a disorder or condition.

The term "therapeutically effective amount" or "effective dose" as used herein refers to an amount of the active ingredient(s) that is(are) sufficient, when administered by a method of the invention, to efficaciously deliver the agents for the treatment of stroke or a cerebrovascular accident.

The term "container" means any receptacle and closure therefor suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

"Concurrent administration," "administered in combination," "simultaneous administration" and similar phrases mean that a composition comprising two or more agents are administered concurrently to the subject being treated. By "concurrently," it is meant that each agent is administered simultaneously or sequentially in any order at different points in time. However, if not administered simultaneously, they are, in one aspect, administered sufficiently closely in time so as to provide the desired treatment effect of the combination of agents. Suitable dosing intervals and dosing order of the agents will: be readily apparent to those skilled in the art. It is also contemplated that two or more agents are administered in separate compositions, and in one aspect, one agent is administered prior to or subsequent to administration of the other agent. Prior administration refers to administration of the agents within the range of one day (24 hours) prior to treatment up to 30 minutes before treatment. It is further contemplated that one agent is administered subsequent to administration of the other agent. Subsequent administration is meant to describe administration from 30 minutes after administration of the other agent up to one day (24 hours) after administration of the first agent. Within 30 minutes to 24 hours may include administration at 30 minutes, 1, 2, 3, 4, 5, 6, 7, 8, 9, 10, 11, 12, 16, 20 or 24 hours.

The use of the terms "a", "an", "the", and similar referents in the context of describing the invention (especially in the context of the claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended merely to better illustrate the invention and is not a limitation on the scope of the invention unless otherwise claimed. No language in the specification should be construed as indicating any non-claimed element as essential to the practice of the invention.

It has been estimated 40 million Americans will be age 65 or older in 2010. An aging population undoubtedly will result in an increased number of cases of chronic diseases, including coronary artery disease, heart failure, and stroke. In addition, an explosive increase in the prevalence of obesity and type 2 diabetes has occurred, and related complications, like hypertension, hyperlipidemia, and atherosclerotic vascular disease, also are expected to increase.

Each year, about 700,000 people experience a new or recurrent stroke. About 500,000 are first attacks and about 200,000 are recurrent attacks. On average, someone in the United States has a stroke every 45 seconds. Also on average, every 3 to 4 minutes someone dies of a stroke. Of all strokes, 87% are ischemic. Intracerebral and subarachnoid hemorrhage strokes account for the remainder. When considered separately from other cardiovascular diseases, stroke ranks third among all causes of death, behind diseases of the heart and cancer. From 1979 to 2004; the number of inpatient discharges from short-stay hospitals with stroke as the first listed diagnosis increased 21% to 906,000. The estimated direct and indirect cost of stroke for 2007 was $62.7 billion.

Each year, about 46,000 more women than men have a stroke. Male stroke incidence rates are greater than female rates at younger ages, but not at older ages. The male/female incidence was 1.25 in those 55 to 64 years of age, 1.50 in those 65 to 74 years of age, 1.07 in those 75 to 84 years of age, and 0.76 in those above 85 years of age. Among American Indians/Alaska natives age 18 and older, 5.1% have had a stroke. Among blacks or African Americans the rate was 3.2%, among whites the rate was 2.5%, and among Asians the rate was 2.4%.

The U.S. Food and Drug Administration (FDA) has approved the clot-dissolving drug tissue plasminogen activator (tPA) to treat strokes caused by blood clots, which cause about 80 percent of all strokes. tPA dissolves the clot and restores blood flow to the brain. tPA carries a risk of bleeding in the brain, but its benefits outweigh the risks when prescribed and administered properly.

It now has been discovered that administration of an $ET_B$ receptor agonist, like IRL-1620, together with an optional, neuroprotective agent, like tissue plasminogen activator, can greatly reduce the neurological deficit in patients suffering from stroke by increasing blood perfusion and reducing damage to the brain.

The methods described herein benefit from the use of an $ET_B$ agonist and an optional neuroprotective agent useful in the treatment and management of strokes and other cerebrovascular accidents. The $ET_B$ receptor agonist and optional neuroprotective agent can be administered simultaneously or sequentially to achieve the desired effect.

The present invention therefore is directed to compositions and methods of treating strokes and other cerebrovascular accidents. The present invention also is directed to pharmaceutical compositions comprising an $ET_B$ receptor agonist and a second therapeutic agent useful in the treatment of strokes and other cerebrovascular accidents, e.g., a neuroprotective agent. Further provided are kits comprising an $ET_B$ receptor agonist and, optionally, a second therapeutic agent useful in the treatment of strokes and other cerebrovascular accidents, packaged separately or together, and an insert having instructions for using these active agents.

As demonstrated below, IRL-1620 increases cerebral blood perfusion and can be used to increase blood perfusion in patients suffering from stroke. IRL-1620 and other $ET_B$ agonists can be particularly useful in treating conditions, like cerebral ischemia, where an increase in cerebral blood flow can help in reducing the penumbra and can greatly reduce the neurological deficits due to stroke.

In accordance with the present invention, it has been found that a selective $ET_B$ receptor agonist, as exemplified by IRL-1620, can be used for the treatment of stroke and other cerebrovasuclar accidents. An $ET_B$ receptor agonist utilized in the present invention is not limited, and can be any $ET_B$ receptor agonist known in the art. Preferably, the $ET_B$ receptor agonist is selective for the $ET_B$ receptor, i.e., is more selective to $ET_B$ receptors than $ET_A$ receptors by a factor of at least $10^3$.

Specific examples of $ET_B$ agonists useful in the present invention include, but are not limited to, IRL-1620, ET-3, sarafotoxin 6c, BQ3020, Ala(1, 3, 11, 15)ET-1, and mixtures thereof. In particular, sarafotoxin 6c (i.e., SFT6C) has an amino acid sequence:

```
                                        (SEQ ID NO: 2)
H-Cys-Thr-Cys-Asn-Asp-Met-Thr-Asp-Glu-Glu-Cys-Leu-

Asn-Phe-Cys-His-Gln-Asp-Val-Ile-Trp-OH;
(Disulfide bridge: 1-15 and 3-11)
``` and a molecular weight of 2515.6.

IRL-1620, also termed N-Succinyl-[Glu$^9$, Ala$^{11,15}$]-Endothelin 1 fragment 8-21, has amino acid sequence Suc-Asp-Glu-Glu-Ala-Val-Tyr-Phe-Ala-His-Leu-Asp-Ile-Ile-Trp (SEQ ID NO: 1); a molecular formula of $C_{86}H_{117}N_{17}O_{27}$; and a molecular weight of 1820.95.

Endothelin 3 (ET-3) has an amino acid sequence of Cys-Thr-Cys-Phe-Thr-Tyr-Lys-Asp-Lys-Glu-Cys-Val-Tyr-Tyr-Cys-His-Leu-Asp-Ile-Ile-Trp [Disulfide Bridges: 1-15; 3-11] (SEQ ID NO: 3); a molecular formula of $C_{121}H_{168}N_{26}O_{33}S_4$; and a molecular weight of 2643.04.

BQ3020, also termed (N-Ac-Ala(11,15)-endothelin-1 (6-21)) and N-Aceytyl-[Ala11,15]-Endothelin 1 fragment 6-21, has an amino acid sequence of Ac-Leu-Met-Asp-Lys-Glu-Ala-Val-Tyr-Phe-Ala-His-Leu-Asp-Ile-Ile-Trp (SEQ ID NO: 4); a molecular formula of $C_{96}H_{140}N_2O_2S_5$; and a molecular weight of 2008.32.

Ala(1,3,11,15)ET-1 (CAS Number 121204-87-3) has an amino acid sequence of Ala-Ser-Ala-Ser-Ser-Leu-Met-Asp-Lys-Glu-Ala-Val-Tyr-Phe-Ala-His-Leu-Asp-Ile-Ile-Trp (SEQ ID NO: 5), a molecular formula of $C_{109}H_{163}N_{25}O_{32}S$; and a molecular weight of 2367.67.

Thus, in one embodiment, the present invention discloses a method of preventing or treating an individual suffering from a stroke or other cerebrovascular accident comprising administering a therapeutically effective amount of an $ET_B$ agonist to the individual. The stroke or cerebrovascular accident can be caused, for example, by thrombosis, embolism, or hemorrhage. In a preferred embodiment, the $ET_B$ receptor agonist comprises N-Succinyl-[Glu$^9$, Ala$^{11,15}$] Endothelin 1 (IRL-1620).

Pharmaceutical compositions containing the $ET_B$ agonist are suitable for administration to humans. Typically, the pharmaceutical compositions are sterile, and contain no toxic, carcinogenic, or mutagenic compounds that would cause an adverse reaction when administered.

The method of the present invention can be accomplished using an $ET_B$ agonist. The $ET_B$ agonist can be administered as the neat compound, or as a pharmaceutical composition. Administration of the pharmaceutical composition, or neat $ET_B$ agonist, can be performed during or after the onset of stroke or other cerebrovascular accident.

The $ET_B$ agonists also can be administered in conjunction with one or more second therapeutic agent useful in the treatment of stroke or other cerebrovascular accident. The second therapeutic agent is different from an $ET_B$ agonist. The $ET_B$ agonist and second therapeutic agent can be administered simultaneously or sequentially. In addition, the $ET_B$ agonist and second therapeutic agent can be administered from a single composition or two separate compositions. Preferred second therapeutic agents comprise a neuroprotective agent.

Nonlimiting examples of second therapeutic agents include, neuroprotective agents like, but are not limited to, a thrombolytic agent (such as, but not limited to, tissue plasminogen activator), an $ET_A$ antagonist (such as, but not limited to, sulfosoxazole, clazosentan, atrasentan, tezosentan, bosentan, sitaxsentan, enrasentan, BMS 207940, BMS 193884, BMS 182874, J 104132, VML 588/Ro 61 1790, T-0115, TAK 044, BQ 788, TBC2576, TBC3214, PD180988, ABT 546, SB247083, RPR118031A, and BQ123), an erythropoiesis-stimulating agent (such as erythropoietin, darbepoetin, and epoetin alfa), or an oxygen carrier (such as, a hemoglobin-based blood substitute or a perfluorocarbon based blood substitute). Other neuroprotective agents that can be administered in combination with the $ET_B$ receptor agonist include, but are not limited to, argatroban, alfimeprase, tenecteplase, ancrod, sildenafil, insulin and its growth factor, magnesium sulfate, human serum albumin, caffeinol (combination of caffeine and alcohol), microplasmin, statins, eptifibatide, tinzaparin, enecadin, citicoline, edaravone, cilostazol, hypothermia, or mixtures thereof.

The neuroprotective agent is administered in an amount to provide its desired therapeutic effect. The effective dosage range for each neuroprotective agent is known in the art, and the neuroprotective agent is administered to an individual in need thereof within such established ranges.

The $ET_B$ receptor agonist and the neuroprotective agent can be administered together as a single-unit dose or separately as multi-unit doses, wherein the $ET_B$ receptor agonist is administered before the neuroprotective agent or vice versa. One or more dose of the $ET_B$ receptor agonist and/or one or more dose of the neuroprotective agent can be administered. It is further contemplated that administration of the agents occurs within 30 minutes up to about one day (24 hours).

An $ET_B$ receptor agonist used in a method present invention can be administered in an amount of about 0.005 to about 500 micrograms per dose, about 0.05 to about 250 micrograms per dose, or about 0.5 to about 50 micrograms per dose. For example, the $ET_B$ agonist can be administered, per dose, in an amount of about 0.005, 0.05, 0.5, 5, 50, or 500 micrograms, including all doses between 0.005 and 500 micrograms.

Alternatively, the $ET_B$ receptor agonist can be administered in an amount of about 0.005 to about 50 micrograms per kilogram per min infusion, or from about 0.05 to about 5 micrograms per kilogram per min infusion. For example, the $ET_B$ agonist can be administered in an amount of about 0.005, 0.05, 0.5, 5, or 50 in micrograms per kilogram per min infusion.

The $ET_B$ agonist can be formulated in suitable excipients for oral administration or for parenteral administration. Such excipients are well known in the art. The $ET_B$ agonists typically are present in such a composition in an amount of about 0.1% to about 75% by weight of the composition.

The $ET_B$ agonists can be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

The pharmaceutical compositions include those wherein the $ET_B$ agonist is administered in an effective amount to achieve its intended purpose. Determination of a therapeutically effective amount is well within the capability of those skilled in the art, especially in light of the detailed disclosure provided herein.

The exact formulation, route of administration, and dosage is determined by an individual physician in view of the patient's condition. Dosage amount and interval can be adjusted individually to provide levels of the $ET_B$ agonist that is sufficient to maintain therapeutic or prophylactic effects. The amount of pharmaceutical composition administered is dependent on the subject being treated, on the subject's weight, the severity of the affliction, the manner of administration, and the judgment of the prescribing physician.

Specifically, for administration to a human in the treatment of stroke or other cerebrovascular accident, oral dosages of an $ET_B$ agonist, individually generally are about 0.005 to about 500 micrograms daily for an average adult patient (70 kg), typically one dose per day or divided into two to three doses per day. Thus, for a typical adult patient, individual doses contain about 0.005 to about 500 micrograms $ET_B$ agonist, in a suitable pharmaceutically acceptable vehicle or carrier, for administration in single or multiple doses, once or several times per day. Dosages for intravenous, buccal, or sublingual administration typically are about 0.005 to about 250 micrograms/kg per single dose as required. In practice, the physician determines the actual dosing regimen that is most suitable for an individual patient, and the dosage varies with the age, weight, and response of the particular patient. The above dosages are exemplary of the average case, but there can be individual instances in which higher or lower dosages are merited, and such are within the scope of this invention.

The $ET_B$ agonists can be administered alone, or in admixture with a pharmaceutical carrier selected with regard to the intended route of administration and standard pharmaceutical practice. Pharmaceutical compositions for use in accordance with the present invention thus can be formulated in a conventional manner using one or more physiologically acceptable carriers comprising excipients and auxiliaries that facilitate processing of the $ET_B$ agonists into preparations that can be used pharmaceutically.

These pharmaceutical compositions can be manufactured in a conventional manner, e.g., by conventional mixing, dissolving, granulating, dragee-making, emulsifying, encapsulating, entrapping, or lyophilizing processes. Proper formulation is dependent upon the route of administration chosen. When a therapeutically effective amount of the $ET_B$ agonists are administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 1% to about 95% of an $ET_B$ agonist, and preferably from about 1% to about 50% $ET_B$ agonist. When administered in liquid form, a liquid carrier, such as water, Petroleum, or oils of animal or plant origin, can be added. The liquid form of the composition can further contain physiological saline solution, dextrose or other saccharide solutions, or glycols. When administered in liquid form, the composition contains about 0.1% to about 90% by weight of $ET_B$ agonists, and preferably about 1% to about 50% of $ET_B$ agonists.

When a therapeutically effective amount of the $ET_B$ agonist is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, an isotonic vehicle. Preferably, the $ET_B$ agonist or composition containing the $ET_B$ agonist is administered by intravenous or bolus injection, or infusion with other fluids over a 10-30 minute span or over several hours.

Suitable $ET_B$ agonists can be readily combined with pharmaceutically acceptable carriers well-known in the art. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding the $ET_B$ agonist to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

The $ET_B$ agonists can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of the $ET_B$ agonists can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

The $ET_B$ agonists also can be formulated in rectal compositions, such as suppositories or retention enemas, e.g., containing conventional suppository bases. In addition to the formulations described previously, the $ET_B$ agonists also can be formulated as a depot preparation. Such long-acting formulations can be administered by implantation (for example, subcutaneously or intramuscularly) or by intramuscular injection. Thus, for example, the $ET_B$ agonists can be formulated with suitable polymeric or hydrophobic materials (for example, as an emulsion in an acceptable oil) or ion exchange resins.

In particular, the $ET_B$ agonists can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. The $ET_B$ agonists also can be injected parenterally, for example, intravenously, intramuscularly, subcutaneously, or intracoronarily. For parenteral administration, the endothelin agonists are best used in the form of a sterile aqueous solution which can contain other substances, for example, salts or monosaccharides, such as mannitol or glucose, to make the solution isotonic with blood.

As an additional embodiment, the invention includes kits which comprise one or more compounds or compositions packaged in a manner that facilitates their use to practice methods of the invention. In one embodiment, the kit includes a compound or composition described herein as useful for practice of a method (e.g., a composition comprising an $ET_B$ agonist and an optional neuroprotective agent), packaged in a container, such as a sealed bottle or vessel, with a label affixed to the container or included in the kit that describes use of the compound or composition to practice the method of the invention Preferably, the compound or composition is packaged in a unit dosage form. The kit further can include a device suitable for administering the composition according to the intended route of administration.

It has been found that an $ET_B$ receptor agonist, like IRL-1620, can treat stroke and other cerebrovascular accidents. Tests and data herein show that $ET_B$ agonists are useful agents to treat stroke and other cerebrovascular accidents.

Experimental Procedures and Results

IRL-1620, a highly selective $ET_B$ receptor agonist, transiently increases tumor blood flow and has been shown to enhance tumor delivery and efficacy of anticancer drugs. A phase 1 clinical trial has recently begun for the use of IRL-1620 in patients with recurrent or progressive carcinoma.

Although known to increase tumor blood flow due to the unique structure of tumor vasculature, the effect of administration of IRL-1620 on other areas of the body that display distinctive vascular structures, specifically the cerebral blood vessels, has not been studied. The present studies were conducted to determine the alteration in cerebral blood flow caused by intravenous administration of the $ET_B$ receptor agonist IRL-1620.

Methods

Male Sprague-Dawley rats weighing 323±4 grams (g) were anesthetized with urethane (ethyl carbamate, Sigma Aldrich, St. Louis, Mo.) dissolved in isotonic saline (0.9% NaCl, Hospira, Inc., Lake Forest, Ill.). The rats were administered a dose of 0.15 g per 100 g body weight via intraperitoneal (i.p.) injection.

Blood Pressure and Heart Rate: The femoral vein and artery were cannulated. The arterial cannula was connected to a Gould P23 ID pressure transducer for recording the blood pressure on a Grass P7D polygraph through a 7PI preamplifier. The heart rate was recorded through a 7P4B Grass tachograph, triggered from blood pressure signals. Drugs were administered via the venous cannula.

Cerebral Perfusion: A burr hole was drilled into the rat skull about 2 millimeters (mm) to the left of midline. Cerebrovascular perfusion was measured via a fiber optic probe (PF407) applied to the surface of the rat brain. The probe was connected to a Periflux PF2b 4000 Laser Doppler Flowmetry unit (Perimed, Stockholm, Sweden).

Renal Perfusion: The right kidney was dissected retroperitoneally. Renal perfusion was measured via a fiber optic probe (PF408) applied to the surface of the rat kidney. The probe was connected to a Periflux PF2b 4000 Laser Doppler Flowmetry unit (Perimed, Stockholm, Sweden).

Blood Gas Analysis: Arterial blood gases were monitored to determine the effects on pH, pCO2, and pO2. Blood was drawn from the arteriole cannula and analyzed using a GEM Premier 3000 unit (Instrument Laboratory, Lexington, Mass.).

Study Design

The rats were randomly selected for various studies. Following surgery the rats were allowed to stabilize for 30 minutes and a 15 minutes baseline recording of all parameters (blood pressure, heart rate, cerebral blood flow, and renal blood flow) was obtained prior to the administration of the pretreatment followed by IRL-1620 (Suc-[Glu 9, Ala 11,15], American Peptide Co, Inc., Sunnyville, Calif.) or ET-1 (Ala 1,3,11,15, RBI Sigma, Natick, Mass.). BQ-788, a selective endothelin B antagonist, is the sodium salt of N-cis-2,6-dimethylpiperidinocarbonyl-L-gamma-methyl-leucyl-D-1-methoxycarbonyl triptophanyl-DNIe (see *Proc. Natl. Acad. Sci. USA*, 91, pp. 4892-4896 (1994)) BMS is BMS 182, 874, which is a selective endothelin A antagonist having a structure

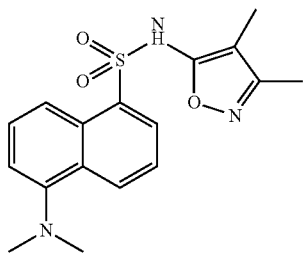 [SMILES: Cc1noc(NS(=O)(=O)c2cccc3c(N(C)C)cccc23)c1C]

Study 1

Group 1: Animals (n=4) were pretreated with saline 15 minutes (min) prior to administration of IRL-1620 (5 µg/kg, i.v.).

Group 2: Animals (n=4) were pretreated with BMS (5 mg/kg, i.v.) 15 min prior to administration of IRL-1620 (5 µg/kg, i.v.).

Group 3: Animals (n=4) were pretreated with BMS (15 mg/kg, i.v.) 15 min prior to administration of IRL-1620 (5 µg/kg, i.v.).

Group 4: Animals (n=4) were pretreated with BQ788 (1 µg/kg, i.v.) 15 min prior to administration of IRL-1620 (5 µg/kg, i.v.).

Study 2

Group 1: Animals (n=4) were pretreated with saline 15 min prior to administration of ET-1 (0.75 µg/kg, i.v.).

Group 2: Animals (n=4) were pretreated with BMS (5 mg/kg, i.v.) 15 min prior to administration of ET-1 (0.75 µg/kg, i.v.).

Group 3: Animals (n=4) were pretreated with BMS (15 mg/kg, i.v.) 15 min prior to administration of ET-1 (0.75 µg/kg, i.v.).

Group 4: Animals (n=4) were pretreated with BQ788 (1 µg/kg, i.v.) 15 min prior to administration of ET-1 (0.75 µg/kg, i.v.).

Blood pressure, heart rate, cerebral blood perfusion, and renal blood perfusion all were recorded for 2 hours following the final injection. Blood gases were analyzed prior to administration of any drugs, and at 60 and 120 min following administration of IRL-1620 or ET-1. At the end of each experiment, the animals were euthanized with an overdose of urethane i.v. In the figures, all data values are presented as mean±SEM. One-sample t-tests and one-way ANOVAs were used to test the differences within and between the groups. A P value of P<0.05 was considered significant.

FIG. 2. shows the effect of IRL-1620 (3 nmol/kg, iv) on cerebral blood perfusion of urethane anesthetized rats using Laser Doppler Flowmetry. IRL-1620 significantly increased cerebral blood perfusion compared to baseline.

Figure 3:
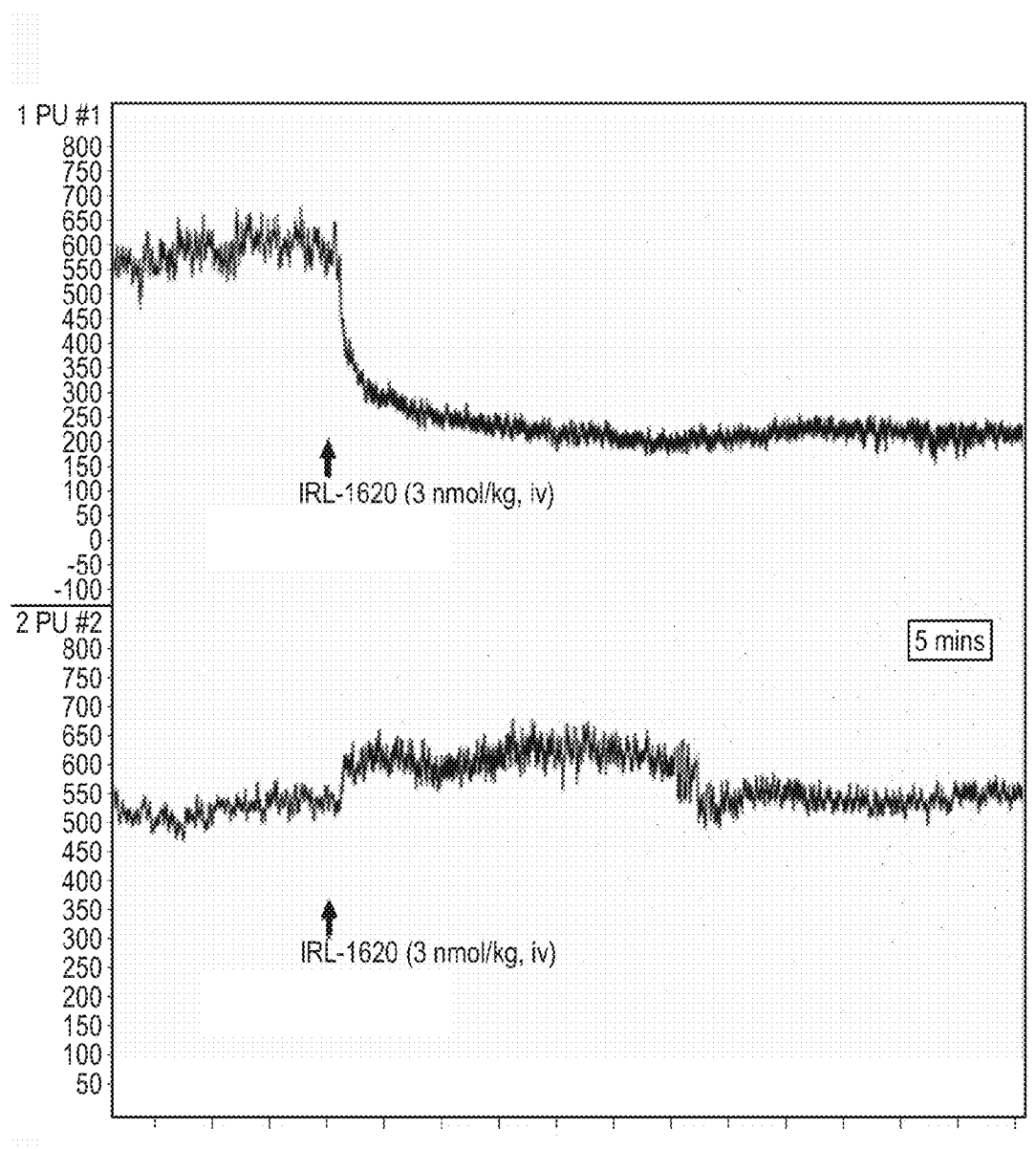
FIG. 3 shows the effect of IRL-1620 (3 nmol/kg, iv) on cerebral and renal blood perfusion of urethane anesthetized rat using Laser Doppler Flowmetry, wherein IRL-1620 significantly increased cerebral blood perfusion and decreased renal blood perfusion compared to baseline.

FIG. 3 shows the effect of IRL-1620 (3 nmol/kg, iv) on cerebral and renal blood perfusion of urethane anesthetized rat using Laser Doppler Flowmetry. IRL-1620 significantly increased cerebral blood perfusion and decreased renal blood perfusion compared to baseline.

Figure 4:
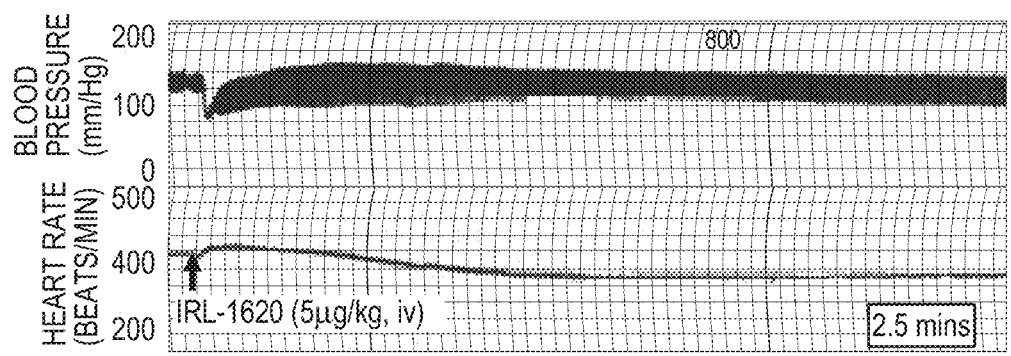
FIG. 4 shows the effect of IRL-1620 (3 nmol/kg, iv or 5 µg/kg, iv) on blood pressure and heart rate of urethane anesthetized rat, i.e., a transient decrease in blood pressure and an increase in heart rate which returned to normal quickly.

FIG. 4 shows the effect of IRL-1620 (3 nmol/kg, iv or 5 µg/kg, iv) on blood pressure and heart rate of urethane anesthetized rat. A transient decrease in blood pressure and an increase in heart rate were observed which returned to normal quickly.

Figure 5:
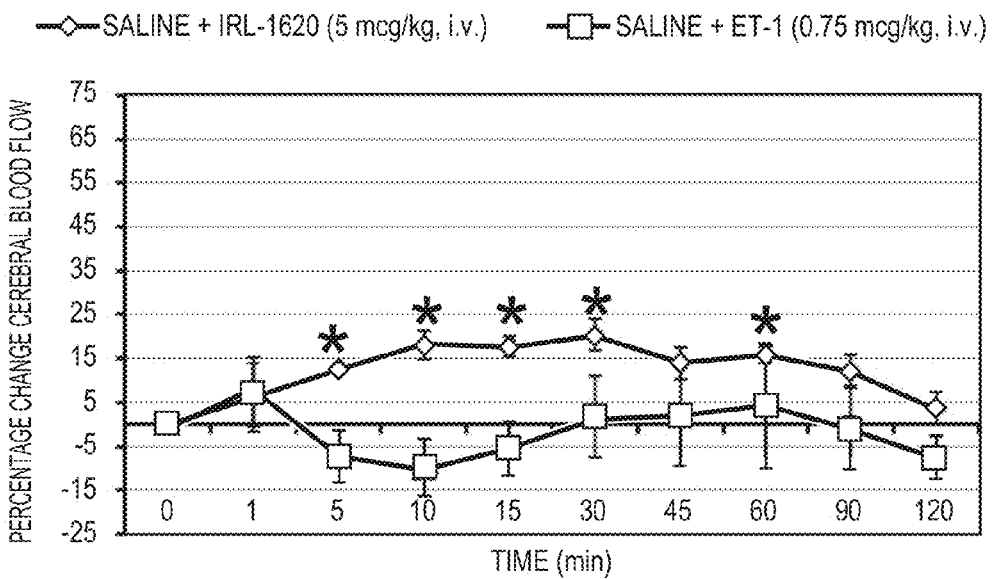
FIG. 5 shows the effect of IRL-1620 (5 µg/kg, i.v.) and ET-1 (0.75 µg/kg, i.v.) on cerebral blood flow, wherein IRL-1620 caused an increase in cerebral blood flow that persisted for about 60 minutes.

FIG. 5 shows the effect of IRL-1620 (5 µg/kg, i.v.) and ET-1 (0.75 µg/kg, i.v.) on cerebral blood flow. IRL-1620 caused an increase in cerebral blood flow of 12.79%, 18.17%, and 17.92% at 5, 10, and 15 min, respectively. This increase persisted for about 60 minutes. ET-1 elicited no significant change in cerebral blood flow.

Figure 6:
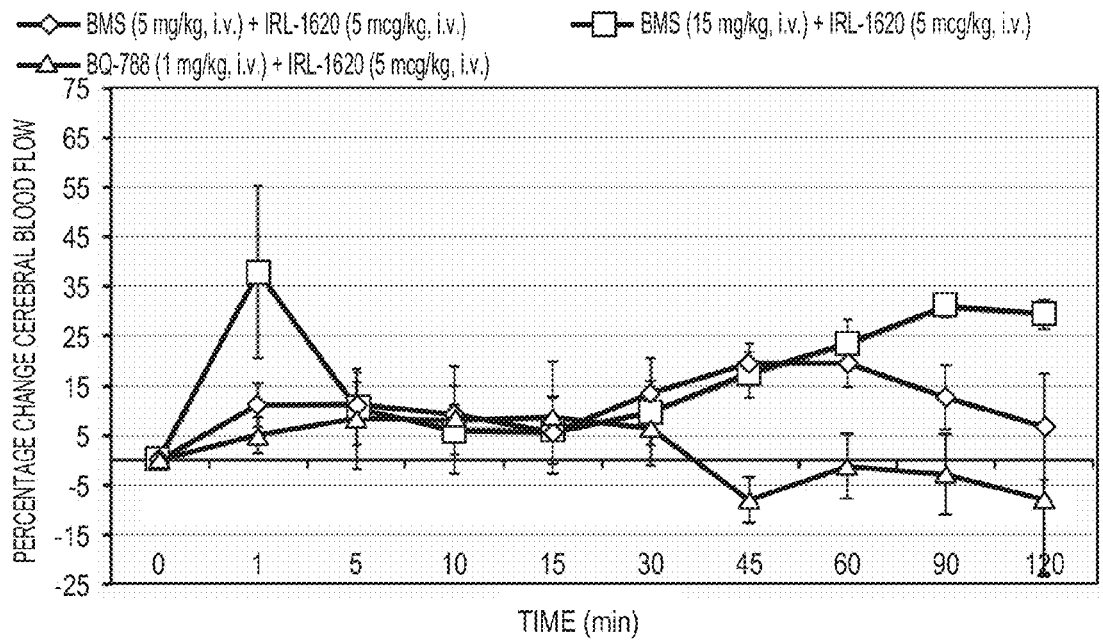
FIG. 6 shows the effect of pretreatment with BMS (5 and 15 mg/kg, i.v.) and BQ788 ($ET_A$ antagonists) (1 µg/kg, i.v.) on the effect of IRL-1620 (5 µg/kg, i.v.) on cerebral blood flow.

FIG. 6 shows the effect of pretreatment with BMS (5 and 15 mg/kg, i.v.) and BQ788 ($ET_A$ antagonists) (1 µg/kg, i.v.) on the effect of IRL-1620 (5 µg/kg, i.v.) on cerebral blood flow. BQ788 effectively blocked the effect of IRL-1620 on cerebral blood flow, while the high dose of BMS caused a transient increase of 37.99% in cerebral blood flow 1 minute after administration of IRL-1620.

Figure 7:
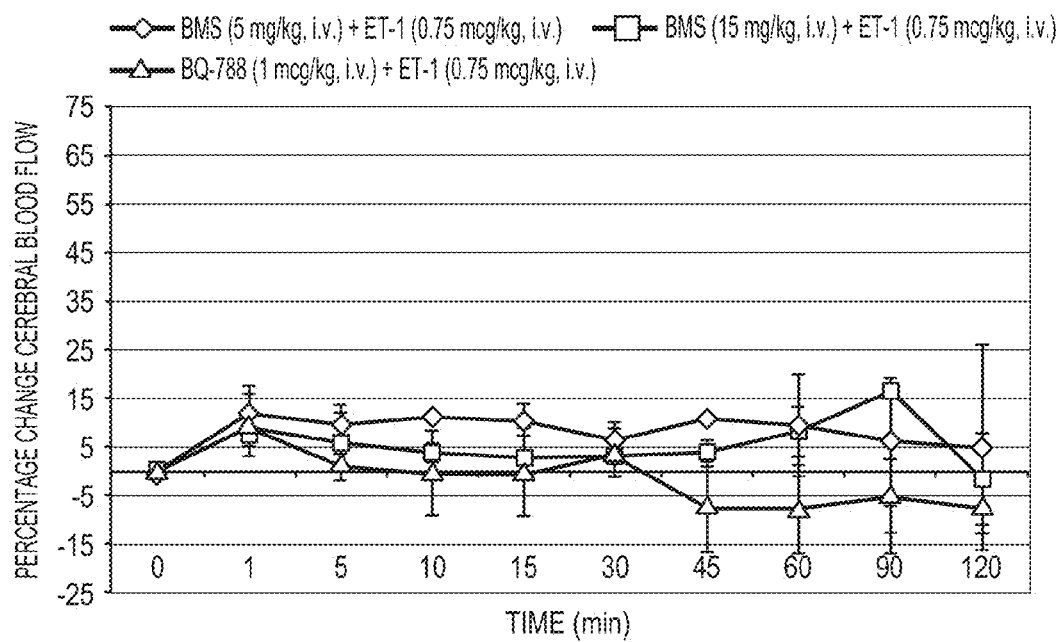
FIG. 7 shows the effect of pretreatment with BMS (5 and 15 mg/kg, i.v.) and BQ788 (1 µg/kg, i.v.) on the effect of ET-1 (0.75 µg/kg, i.v.) on cerebral blood flow.

FIG. 7 shows the effect of pretreatment with BMS (5 and 15 mg/kg, i.v.) and BQ788 (1 µg/kg, i.v.) on the effect of ET-1 (0.75 µg/kg, i.v.) on cerebral blood flow. Pretreatment with the $ET_A$ antagonists produced no significant change to the effect of ET-1 on cerebral blood flow.

Figure 8:
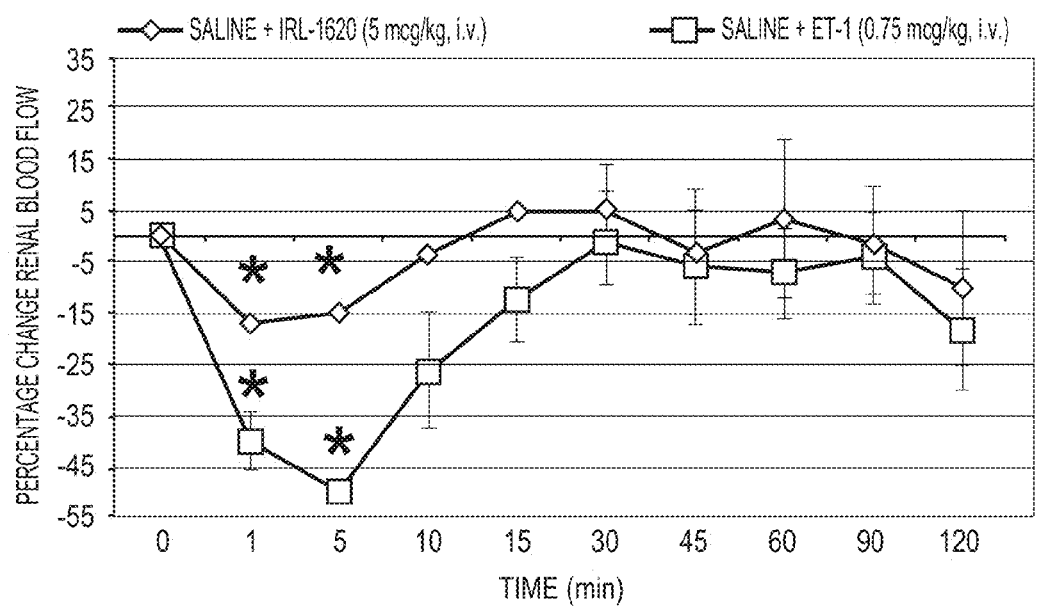
FIG. 8 shows the effect of IRL-1620 (5 µg/kg, i.v.) and ET-1 (0.75 µg/kg, i.v.) on renal blood flow, wherein IRL-1620 elicited a decrease in renal blood flow that persisted for about 15 minutes.

FIG. 8 shows the effect of IRL-1620 (5 µg/kg, i.v.) and ET-1 (0.75 µg/kg, i.v.) on renal blood flow. IRL-1620 elicited a decrease in renal blood flow of 16.94%, 15.05%, and 3.85% at 1, 5, and 10 minutes, respectively. This decrease persisted for approximately 15 minutes. ET-1 elicited a decrease in renal blood flow of 40.27%, 50.10%, and 26.33% at 1, 5, and 10 minutes, respectively. This decrease in renal blood flow also persisted for about 15 minutes before returning to basal levels.

Figure 9:
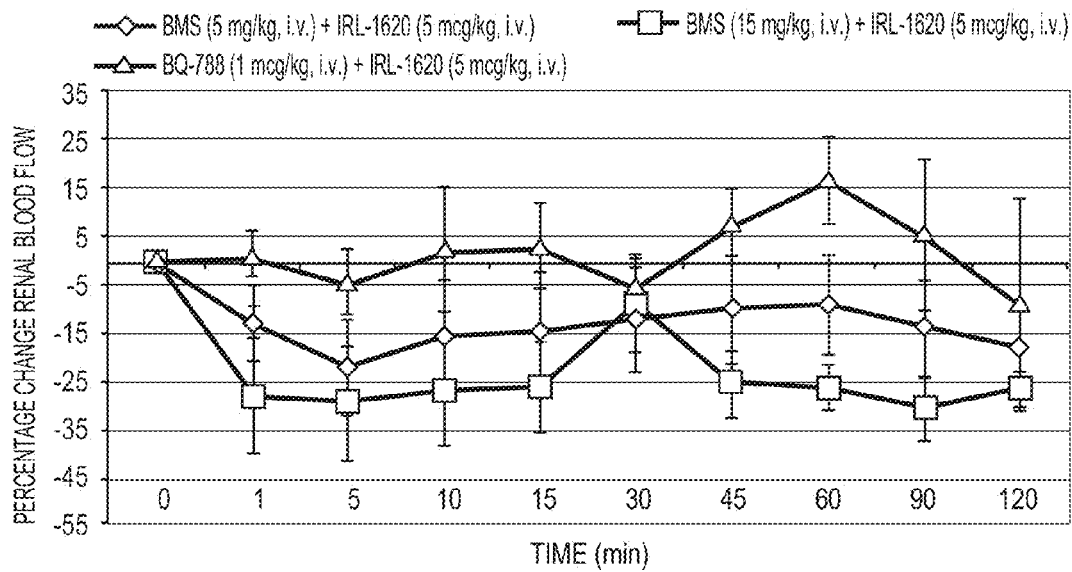
FIG. 9 shows the effect of pretreatment with BMS (5 and 15 mg/kg, i.v.) and, BQ788 (1 µg/kg, i.v.) on the effect of IRL-1620 (5 µg/kg, i.v.) on renal blood flow.

FIG. 9 shows the effect of pretreatment with BMS (5 and 15 mg/kg, i.v.) and BQ788 (1 µg/kg, i.v.) on the effect of IRL-1620 (5 µg/kg, i.v.) on renal blood flow. BQ788 effectively blocked the effect of IRL-1620 on renal blood flow, while the BMS caused a sustained decrease in renal blood flow up to 120 minutes after IRL-1620 administration.

Figure 10:
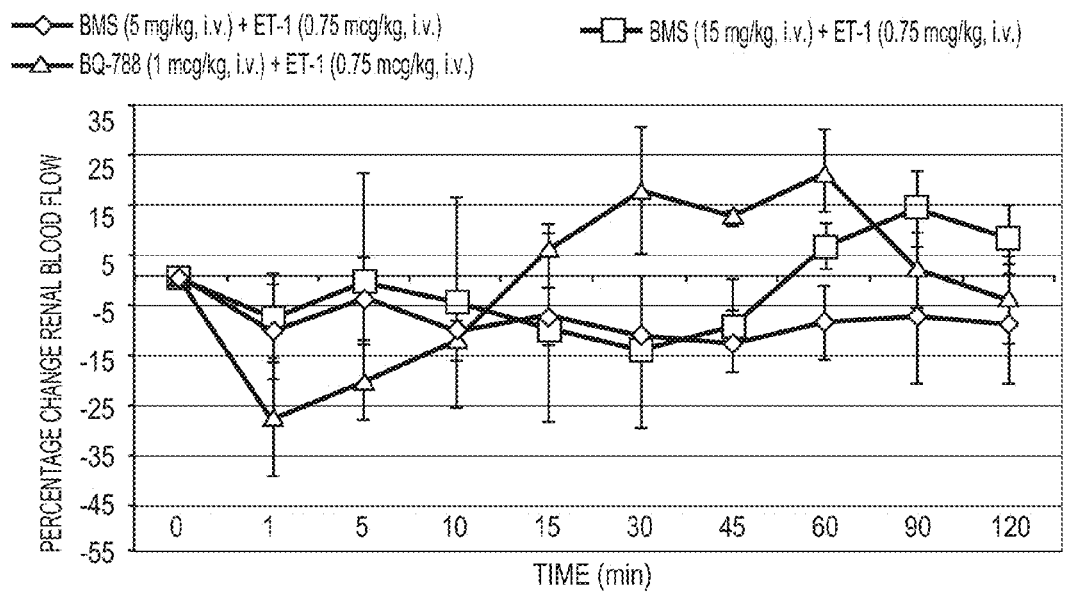
FIG. 10 shows the effect of pretreatment with BMS (5 and 15 mg/kg, i.v.) and BQ788 (1 µg/kg, i.v.) on the effect of ET-1 (0.75 µg/kg, i.v.) on renal blood flow, wherein no pretreatment significantly altered the effect of ET-1 on renal blood flow.

FIG. 10 shows the effect of pretreatment with BMS (5 and 15 mg/kg, i.v.) and BQ788 (1 µg/kg, i.v.) on the effect of ET-1 (0.75 µg/kg, i.v.) on renal blood flow. No pretreatment significantly altered the effect of ET-1 on renal blood flow.

Figure 11:
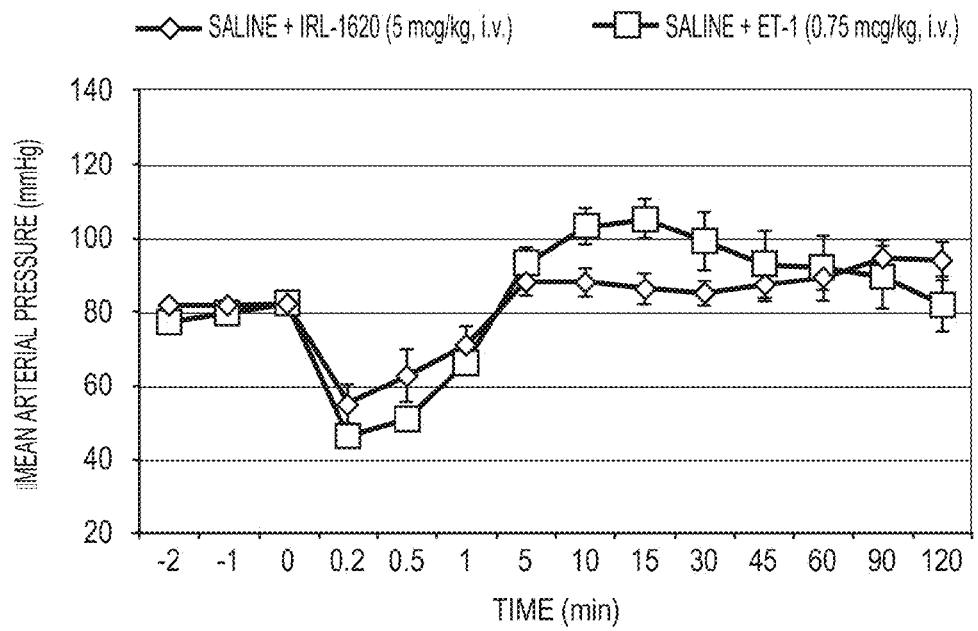
FIG. 11 shows the effect of administration of IRL-1620 (5.0 µg/kg, i.v.) and ET-1 (0.75 µg/kg, i.v.) on mean arterial pressure.
Figure 12:
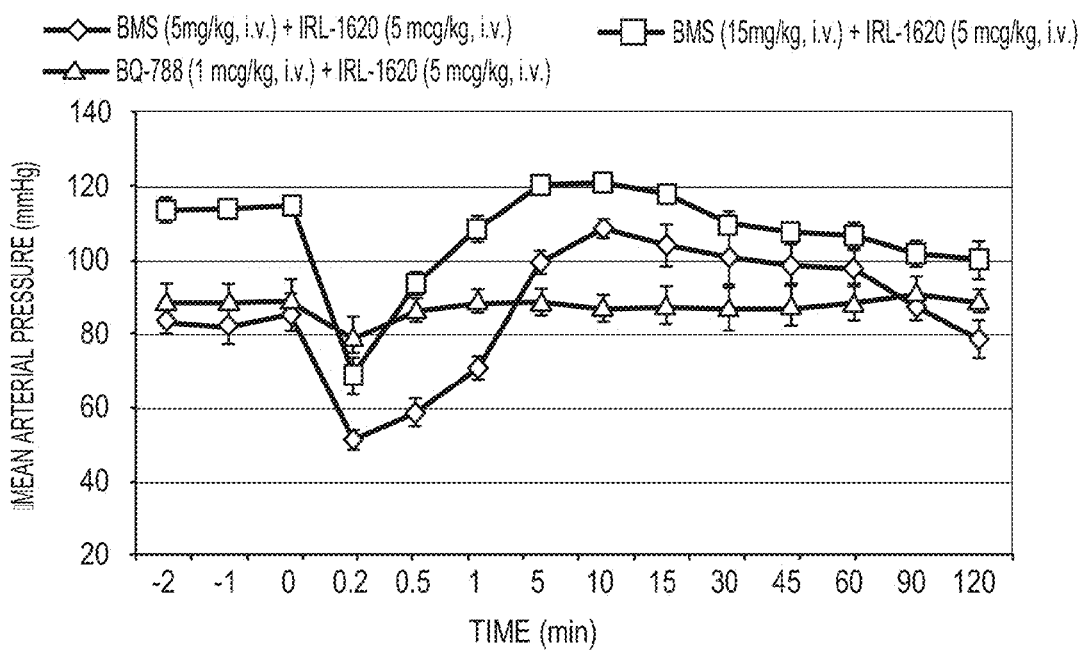
FIG. 12 shows the effect of pretreatment with BMS (5 and 15 mg/kg, i.v.) and BQ788 (1 µg/kg, i.v.) on the effect of IRL-1620 (5 µg/kg, i.v.) on mean arterial pressure.

FIG. 11 shows the effect of administration of IRL-1620 (5.0 µg/kg, i.v.) and ET-1 (0.75 µg/kg, i.v.) on mean arterial pressure. Mean arterial pressure decreased 33.32%, 23.88%, and 13.66% at 0.2, 0.5, and 1 minute following administration of IRL-1620. Mean arterial pressure decreased 43.16%, 37.80%, and 19.30% at 0.2, 0.5, and 1 minute, respectively, following ET-1 administration. The subsequent hypertension following ET-1 administration was recorded as an increase in mean arterial pressure of 12.72%, 25.56% and 28.49% at 5, 10, and 15 minutes, respectively FIG. 12 shows the effect of pretreatment with BMS (5 and 15 mg/kg, i.v.) and BQ788 (1 µg/kg, i.v.) on the effect of IRL-1620 (5 µg/kg, i.v.) on mean arterial pressure. BQ788 effectively blocked the effect of IRL-1620 on mean arterial pressure, while pretreatment with both doses of BMS produced transient hypotension similar to that observed in animals pretreated with saline.

Figure 13:
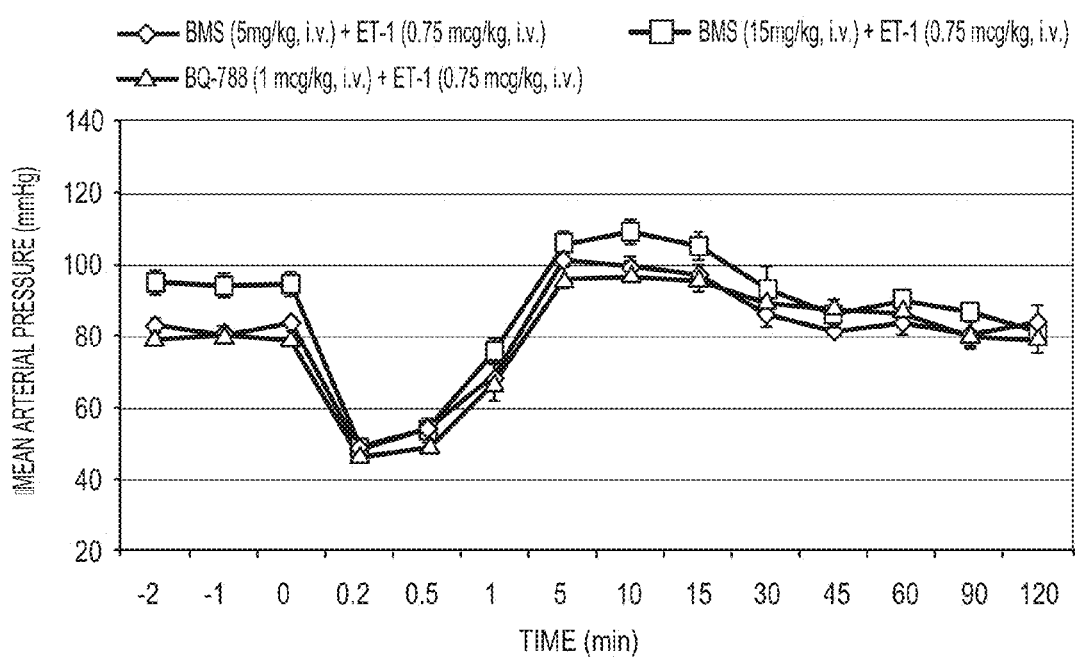
FIG. 13 shows the effect of pretreatment with BMS (5 and 15 mg/kg, i.v.) and BQ788 (1 µg/kg, i.v.) on the effect of ET-1 (0.75 µg/kg, i.v.) on mean arterial pressure, wherein pretreatment with BQ788 and BMS failed to alter the effect of ET-1 on mean arterial pressure.

FIG. 13 shows the effect of pretreatment with BMS (5 and 15 mg/kg, i.v.) and BQ788 (1 µg/kg, i.v.) on the effect of ET-1 (0.75 µg/kg, i.v.) on mean arterial pressure. Pretreatment with BQ788 and BMS failed to alter the effect of ET-1 on mean arterial pressure.

The following Table 1 shows the effect of IRL-1620 (5 µg/kg, i.v.) on heart rate. The values are expressed as mean±SEM. Administration of IRL-1620 when animals were pretreated with either saline or BMS (5 and 15 mg/kg) caused an increase in heat rate. Pretreatment with BQ788 effectively blocked the effect of IRL-1620 on heart rate. No significant alteration in heart rate was seen after administration of ET-1, with or without pretreatment.

TABLE 1

| Time (min) Pretreatment | 0 | 1 | 5 | 10 | 15 | 30 | 45 | 60 | 90 | 120 |
|---|---|---|---|---|---|---|---|---|---|---|
| Saline | 352 ± 3 | 368 ± 6 | 351 ± 5 | 351 ± 4 | 353 ± 4 | 360 ± 3 | 370 ± 2 | 379 ± 3 | 392 ± 2 | 382 ± 8 |
| 1 µg/kg BQ788 | 344 ± 5 | 350 ± 6 | 345 ± 4 | 345 ± 4 | 347 ± 3 | 347 ± 4 | 350 ± 6 | 351 ± 9 | 351 ± 13 | 353 ± 13 |
| 5 mg/kg BMS | 339 ± 6 | 365 ± 4 | 357 ± 13 | 345 ± 14 | 345 ± 14 | 356 ± 12 | 367 ± 14 | 370 ± 14 | 350 ± 9 | 327 ± 12 |
| 15 mg/kg BMS | 405 ± 11 | 425 ± 11 | 382 ± 13 | 380 ± 11 | 384 ± 11 | 387 ± 17 | 387 ± 21 | 395 ± 19 | 393 ± 21 | 386 ± 18 |

The following Table 2 shows the effect of IRL-1620 and ET-1 on arterial blood gases. Neither IRL-1620 nor ET-1 significantly affected blood gases.

TABLE 2

| | pH | | | pO2 | | | pCO2 | | |
|---|---|---|---|---|---|---|---|---|---|
| Time (min) | 0 | 60 | 120 | 0 | 60 | 120 | 0 | 60 | 120 |
| IRL-1620 (5 µg/kg, i.v.) | 7.32 ± 0.01 | 7.27 ± 0.01 | 7.29 ± 0.01 | 103 ± 3 | 99 ± 9 | 113 ± 6 | 42 ± 2 | 46 ± 6 | 32 ± 3 |
| ET-1 (0.75 µg/kg, i.v.) | 7.32 ± 0.01 | 7.29 ± 0.01 | 7.27 ± 0.01 | 118 ± 4 | 110 ± 2 | 116 ± 5 | 34 ± 3 | 40 ± 4 | 38 ± 4 |

The above tests and data show that administration of IRL-1620 produces a significant increase in cerebral blood perfusion lasting about 60 minutes. This effect can be blocked via pretreatment with $ET_A$ receptor antagonist BQ-788.

---

The invention claimed is:

1. A method of reducing damage to a brain cell caused by lack of blood supply or lack of oxygenation to the brain cell comprising administering a therapeutically effective amount of N-Succinyl-[Glu$^9$, Ala$^{11,15}$] Endothelin 1 to an individual in need thereof, wherein the administering comprises multiple dose administration of N-Succinyl-[Glu$^9$, Ala$^{11,15}$] Endothelin 1.

2. The method of claim 1 further comprising administering a therapeutically effective amount of a second therapeutic agent useful in reducing damage to the brain cell.

3. The method of claim 2 wherein the second therapeutic agent comprises a neuroprotective agent.

4. The method of claim 3 wherein the neuroprotective agent is selected from the group consisting of a thrombolytic agent, an erythropoiesis-stimulating agent, an Endothelin A (ET$_A$) antagonist, an oxygen carrier, and mixtures thereof.

5. The method of claim 4 wherein the thrombolytic agent comprises tissue plasminogen activator.

6. The method of claim 4 wherein the erythropoiesis-stimulating agent is selected from the group consisting of erythropoietin, darbepoetin, epoetin alfa, and mixtures thereof.

7. The method of claim 4 wherein the oxygen carrier comprises a hemoglobin-based blood substitute, a perfluorocarbon-based blood substitute, or a mixture thereof.

8. The method of claim 4 wherein the ET$_A$ antagonist is selected from sulfosoxazole, clazosentan, atrasentan, tezosentan, bosentan, sitaxsentan, enrasentan, BMS 207940, BMS 193884, BMS 182874, J 104132, VML 588/Ro 61 1790, T-0115, TAK 044, BQ 788, TBC2576, TBC3214, PD180988, ABT 546, SB247083, RPR118031A, BQ123, and mixtures thereof.

9. The method of claim 3 wherein the neuroprotective agent is selected from the group consisting of argatroban, alfimeprase, tenecteplase, ancrod, sildenafil, insulin, insulin growth factor, magnesium sulfate, human serum albumin, caffeinol, microplasmin, a statin, eptifibatide, tinzaparin, enecadin, citicoline, edaravone, cilostazol, and mixtures thereof.

10. The method of claim 2 wherein the N-Succinyl-[Glu$^9$, Ala$^{11,15}$] Endothelin 1 and the second therapeutic agent are administered simultaneously.

11. The method of claim 10 wherein the N-Succinyl-[Glu$^9$, Ala$^{11,15}$] Endothelin 1 and the second therapeutic agent are administered from a single composition.

12. The method of claim 10 wherein the N-Succinyl-[Glu$^9$, Ala$^{11,15}$] Endothelin 1 and the second therapeutic agent are administered from separate compositions.

13. The method of claim 2 wherein the N-Succinyl-[Glu$^9$, Ala$^{11,15}$] Endothelin 1 and the second therapeutic agent are administered separately.

14. The method of claim 2 wherein the N-Succinyl-[Glu$^9$, Ala$^{11,15}$] Endothelin 1 is administered prior to the second therapeutic agent.

15. The method of claim 13 wherein the N-Succinyl-[Glu$^9$, Ala$^{11,15}$] Endothelin 1 is administered in an amount of about 0.005 to about 500 micrograms per dose.

16. The method of claim 1 wherein the N-Succinyl-[Glu$^9$, Ala$^{11,15}$] Endothelin 1 is administered in an amount of about 0.005 to about 50 micrograms per kilogram per min infusion.

17. The method of claim 1 wherein about 0.5 micrograms per kilogram (μg/kg) of the N-Succinyl-[Glu$^9$, Ala$^{11,15}$] Endothelin 1 is administered intravenously per dose.

18. The method of claim 17 wherein the N-Succinyl-[Glu$^9$, Ala$^{11,15}$] Endothelin 1 is administered in three doses per day.

* * * * *

UNITED STATES PATENT AND TRADEMARK OFFICE
CERTIFICATE OF CORRECTION

PATENT NO. : 9,493,524 B2  
APPLICATION NO. : 14/149785  
DATED : November 15, 2016  
INVENTOR(S) : Anil Gulati Page 1 of 1

It is certified that error appears in the above-identified patent and that said Letters Patent is hereby corrected as shown below:

In the Claims

At Column 22, Line 18, "claim 2" should be -- claim 13 --.

At Column 22, Line 21, "claim 13" should be -- claim 1 --.

Signed and Sealed this
Sixth Day of June, 2017

Michelle K. Lee
*Director of the United States Patent and Trademark Office*